(12) United States Patent
Palumbo et al.

(10) Patent No.: US 12,582,664 B2
(45) **Date of Patent: *Mar. 24, 2026**

(54) TREATMENT OF FRAGILE X SYNDROME WITH CANNABIDIOL

(71) Applicant: Harmony Biosciences Management, Inc., Plymouth Meeting, PA (US)

(72) Inventors: Joseph Palumbo, Saint Davids, PA (US); Stephen V. O'Quinn, Wake Forest, NC (US); Terri Sebree, Gladwyne, PA (US); Marcel Bonn-Miller, Lexington, NC (US); Donna Gutterman, Raleigh, NC (US)

(73) Assignee: Harmony Biosciences Management, Inc., Plymouth Meeting, PA (US)

( * ) Notice: Subject to any disclaimer, the term of this patent is extended or adjusted under 35 U.S.C. 154(b) by 213 days.

This patent is subject to a terminal disclaimer.

(21) Appl. No.: 17/970,395

(22) Filed: Oct. 20, 2022

(65) Prior Publication Data

US 2023/0059709 A1     Feb. 23, 2023

Related U.S. Application Data

(63) Continuation-in-part of application No. 17/465,141, filed on Sep. 2, 2021, now abandoned, which is a continuation of application No. 16/737,326, filed on Jan. 8, 2020, now abandoned, which is a continuation of application No. 16/411,248, filed on May 14, 2019, now Pat. No. 10,568,848, which is a continuation of application No. 16/220,249, filed on Dec. 14, 2018, now Pat. No. 10,314,792, which is a continuation of application No. 16/144,632, filed on Sep. 27, 2018, now Pat. No. 10,213,390.

(60) Provisional application No. 63/271,015, filed on Oct. 22, 2021, provisional application No. 62/632,532, filed on Feb. 20, 2018, provisional application No. 62/564,834, filed on Sep. 28, 2017.

(51) Int. Cl.
| | |
|---|---|
| *A61K 31/05* | (2006.01) |
| *A61K 9/00* | (2006.01) |
| *A61K 9/06* | (2006.01) |
| *A61K 31/00* | (2006.01) |
| *A61K 36/185* | (2006.01) |
| *A61P 25/00* | (2006.01) |

(52) U.S. Cl.
CPC .......... *A61K 31/658* (2023.05); *A61K 9/0014* (2013.01); *A61K 9/06* (2013.01); *A61K 36/3482* (2024.05); *A61P 25/00* (2018.01)

(58) Field of Classification Search
None
See application file for complete search history.

(56) References Cited

U.S. PATENT DOCUMENTS

| | | | |
|---|---|---|---|
| 7,423,026 | B2 | 9/2008 | Jarvinen et al. |
| 9,943,491 | B2 | 4/2018 | De Vries et al. |
| 10,213,390 | B1 | 2/2019 | Bonn-Miller et al. |
| 10,314,792 | B2 | 6/2019 | Sebree et al. |
| 10,471,022 | B2 | 11/2019 | Bonn-Miller et al. |
| 10,716,766 | B2 | 7/2020 | Aung-Din |
| 10,758,497 | B2 | 9/2020 | Bonn-Miller et al. |
| 11,458,109 | B2 | 10/2022 | Sebree et al. |
| 11,458,110 | B2 | 10/2022 | Bonn-Miller et al. |
| 11,779,549 | B2 | 10/2023 | Bonn-Miller et al. |
| 12,186,282 | B2 | 1/2025 | Sebree et al. |
| 12,213,951 | B2 | 2/2025 | Sebree et al. |
| 12,226,373 | B2 | 2/2025 | Bonn-Miller et al. |
| 2008/0139472 | A1* | 6/2008 | Lauterborn ........ A61K 31/5365 514/249 |
| 2016/0000843 | A1 | 1/2016 | Lowe et al. |
| 2017/0231923 | A1 | 8/2017 | Guy et al. |
| 2017/0348276 | A1 | 12/2017 | Bryson et al. |
| 2019/0117619 | A1 | 4/2019 | Guy et al. |
| 2020/0214995 | A1 | 7/2020 | Sebree et al. |
| 2021/0196669 | A1 | 7/2021 | Bar-Lev Schleider et al. |
| 2021/0369643 | A1 | 12/2021 | Sebree et al. |
| 2021/0401769 | A1 | 12/2021 | Griesser et al. |
| 2022/0096396 | A1 | 3/2022 | Sebree et al. |
| 2023/0000792 | A1 | 1/2023 | Sebree et al. |
| 2023/0000793 | A1 | 1/2023 | Sebree et al. |
| 2023/0059709 | A1 | 2/2023 | Palumbo et al. |

(Continued)

FOREIGN PATENT DOCUMENTS

| | | | |
|---|---|---|---|
| AU | 2018101357 | A4 | 10/2018 |
| CN | 105517546 | A | 4/2016 |

(Continued)

OTHER PUBLICATIONS

Khalil, Rami Bou, "Would some cannabinoids ameliorate symptoms of autism?", European Child & Adolescent Psychiatry, 21(4):237-238, XP035037636, ISSN: 1435-165X, DOI: 10.1007/S00787-012-0255-Z (2017).

Anonymous: History of Changes for Study: NCT02956226, "Cannabinoids for Behavioral Problems in Children with ASD (CBA)", XP055718101, Retrieved from the Internet: URL:https://clinicaltrials.gov/ct2/history/NCT02956226?V_4=View#StudyPage Top [retrieved on Jul. 27, 2020] (2017).

Hammell, D.C., et al., "Transdermal cannabidiol reduces inflammation and pain-related behaviours in a rat model of arthritis", Eur. J. Pain, vol. 20(6): 936-948. doi: 10.1002/ejp.818 (Jul. 2016).

Extended European Search Report for EP21206188, mailed Feb. 3, 2022, 9 pages.

(Continued)

*Primary Examiner* — Michael V Meller

(74) *Attorney, Agent, or Firm* — WOMBLE BOND DICKINSON (US) LLP; Danielle L. Herritt; Mark R. Deluca

(57) ABSTRACT

The present technology relates to a method of treating one or more behavioral symptoms of autism spectrum disorder (ASD) in a subject by administering an effective amount of cannabidiol (CBD). Specifically, subjects having moderate to severe ASD and relatively high social avoidance and/or anxiety are more likely to show a reduction in irritability when treated with CBD.

15 Claims, 1 Drawing Sheet

(56) References Cited

U.S. PATENT DOCUMENTS

| | | |
|---|---|---|
| 2023/0414533 A1 | 12/2023 | Bonn-Miller et al. |
| 2024/0122873 A1 | 4/2024 | Griesser et al. |
| 2024/0342198 A1 | 10/2024 | Palumbo et al. |
| 2025/0134832 A1 | 5/2025 | Sebree et al. |
| 2025/0134833 A1 | 5/2025 | Bonn-Miller et al. |
| 2025/0177322 A1 | 6/2025 | Bonn-Miller et al. |
| 2025/0205174 A1 | 6/2025 | Sebree et al. |

FOREIGN PATENT DOCUMENTS

| | | |
|---|---|---|
| CN | 107126411 A | 9/2017 |
| GB | 2549278 A | 10/2017 |
| WO | 2006133941 A2 | 12/2006 |
| WO | 2016141056 A1 | 9/2016 |
| WO | 2017068349 A1 | 4/2017 |
| WO | 2018011808 A1 | 1/2018 |
| WO | 2019034985 A1 | 2/2019 |
| WO | 2019089583 A1 | 5/2019 |
| WO | 2022017942 A1 | 1/2022 |
| WO | 2022103638 A1 | 5/2022 |

OTHER PUBLICATIONS

Heussler, Helen et al., "A phase 1/2, open-label assessment of the safety, tolerability, and efficacy of transdermal cannabidiol (ZYN002) for the treatment of pediatric fragile X syndrome", Journal of Neurodevelopmental Disorders, vol. 11, No. 1, pp. 1-9, XP055828347 (2019).

Hagerman, Randi, et al., "Fragile X Syndrome and Targeted Treatment Trials", National Institutes of Health Public Access Manuscript, published as Results Probl Cell Differ., vol. 54:297-335. doi:10.1007/978-3-642-21649-7_17 (2012).

Kaufmann, Walter E., et al., "Autism Spectrum Disorder in Fragile X Syndrome: Cooccurring Conditions and Current Treatment", HHS Public Access Manuscript, published as Pediatrics, vol. 139(Suppl 3):S194-S206. doi:10.1542/peds.2016-1159F (2017).

Mechoulam, Raphael, et al., "Cannabidiol: An Overview of Some Pharmacological Aspects", The Journal of Clinical Pharmacology, vol. 42, Issue 51, p. 11S-19S (2002).

Pisante, S., et al., "Cannabidiol: State of the Art and New Challenges for Therapeutic Applications", Pharmacology and Therapeutics, vol. 175, pp. 133-150 (2017).

Mechoulam, Raphael, et al., "Cannabidiol - Recent Advances", Chemistry & Biodiversity; vol. 4, pp. 1678-1692 (2007).

Belmonte, Matthew K., et al., "Fragile X syndrome and autism at hte intersection of genetic and neural networks", Nature Neuroscience, vol. 9(10):1221-1225 (2006).

Zynerba Pharmaceuticals Announces Top-Line Results from Phase 2 STAR 1 Trial of ZYN002 in Adult Epilepsy Patients with Focal Seizures (Aug. 7, 2017).

Hagerman, Randi J., et al., "Fragile X-Associated Neuropsychiatric Disorders (FXAND)," Frontiers in Psychiatry, vol. 9. Article 564, pp. 1-9 (2018).

Crawford, Dana C., et al., "FMR1 and the Fragile X Syndrome: Human Genome Epidemiology Review," Genet. Med., Author manuscript, HHS Public Access, vol. 3(5):359-371 (2001).

Godler, David Eugeny, et al., "Methylation of novel markers of fragile X alleles is inversely correlated with FMRP expression and FMR1 activation ratio," Human Molecular Genetics, vol. 9(18):1618-1632 (2010).

Sdcaadmin, "The Difference Between Moderate to Severe Autism," Sarah Dooley Center for Autism, pp. 1-6 (2019).

Aran, Adi, et al., "Brief Report: Cannabidiol-Rich Cannabis in Children with Autism Spectrum Disorder and Severe Behavioral Problems-A Retrospective Feasibility Study," Journal of Autism and Developmental Disorders, vol. 49:1284-1288 (2019).

Hagerman, Randi J., et al., "High Functioning Fragile X Males: Demonstration of an Unmethylated Fully Expanded FMR-1 Mutation Associated with Protein Expression," American Journal of Medical Genetics, vol. 51:298-308 (1994).

Ali, Shayma et al., "Efficacy of cannabinoids in paediatric epilepsy", Developmental Medicine & Child Neurology, vol. 61:13-18 (2019).

Kuchenbuch, Mathieu, et al., "Add-on cannabidiol significantly decreases seizures in 3 patients with SYNGAP1 developmental and epileptic encephalopathy," Epilepsia Open, vol. 5:496-500 (2020).

SynGAP Research Fund, Webinar, CBD, Seizures & SynGAP: Parents Experience (2019).

Vlaskamp, Danique R.M., et al., "SYNGAP1 encephalopathy: A distinctive generalized developmental and epileptic encephalopathy," Neurology, vol. 92(2):e96-e107 (2019).

"Lacking guidance from doctors, parents lead the charge in treating children with CBD," Peninsula Press (2018).

Salcedo-Arellano, Maria Jimena, et al., "Overlapping Molecular Pathways Leading to Autism Spectrum Disorders, Fragile X Syndrome, and Targeted Treatments", Neurotherapeutics, Springer International Publishing, Cham, vol. 18, No. 1, pp. 265-283 (2020).

International Search Report and Written Opinion for corresponding PCT/US2022/078449 mailed Feb. 2, 2023, 13 pages.

Hagerman, Paul J., Ph.D., M.D et al., Fragile X Syndrome: Diagnosis, Treatment, and Research, The Johns Hopkins University Press, pp. 210, 213, 471 and 472, 3rd Edition (2002).

Liu, X. Shawn, et al., Rescue of Fragile X Syndrome Neurons by DNA Methylation Editing of the FRM1 Gene, Cell Press, vol. 172:979-992 (2018).

Payan Gomez, Cesar, et al., "Variable Expressivity in Fragile X Syndrome: Towards the Identification of Molecular Characteristics That Modify the Phenotype", The Application of Clinical Genetics, DovePress, vol. 14:305-312 (2021).

Clinical Leader: Zynerba Pharmaceuticals Achieves Target Enrollment in Exploratory Phase 2 Trial of ZYN002 in Fragile X Syndrome, retrieved from the internet at URL: < https://www.clinicalleader.com/doc/zynerba-pharmaceuticals-achieves-target-exploratoryphase-syndrome-0001>, retrieved on Aug. 31, 2023 (2017).

Buckner, Julia D., et al., "Cannabis-related impairment and social anxiety: the roles of gender and cannabis use motives", Addictive Behaviors, vol. 37(11): 1294-1297 (2012).

Fung, Wai Lun Alan, et al., "Elevated Prevalence of Generalized Anxiety Disorder in Adults 22q11.2 Deletion Syndrome", American Journal of Psychiatry, vol. 167(8):998, XP009553437 (2010).

Siegel, Steven, et al., Transdermal Cannabidiol (CBD) Gel for the Treatment of Fragile X Syndrome (Fxs), ACNP 57th Annual Meeting: Poster Session III, Neuropsychopharmacology, vol. 43, Suppl. 1, pp. S399-S400, XP093109132 (2018).

Maneeton, Narong, et al., "Risperidone for children and adolescents with autism spectrum disorder: a systematic review", Neuropsychiatric Disease and Treatment, vol. 14:1811-1820 (2018).

National Library of Medicine; Natonal Center for Biotechnology Information; PubChem; Compound Summary—Cannabidiol; 67 pages (2014).

International Preliminary Report on Patentability for corresponding PCT/US2022/078449 dated Apr. 23, 2024, 9 pages.

Tartaglia, Nicole, et al., "Treatment of Fragile X Syndrome with Cannabidiol: A Case Series Study and Brief Review of the Literature", Cannabis and Cannabinoid Research, vol. 4(1):3-9 (2019).

Heussler, H. et al., "Transdermal cannabidiol (CBD) Gel for the treatment of fragile X syndrome (FXS)", 57th Annual Meeting of the American College of Neuropsychopharmacology (ACNP), Hollywood, FL. 2018, Poster P5-092, <URL: https://www.zynerba.com/wp-content/uploads/2019/05/Transdermal-Cannabidiol-CBD-Gel-for-the-Treatment-of-Fragile-X-Syndrome.pdf>.

Deng, Ming Yu, et al., "New Progress of Clinical Research to Autistic Spectrum Disorder" (DSM-5 Update).

Saul, Robert A., MD, FACMG, et al., FMR1 (FMR1-Related Disorders), Gene Reviews Japan, pp. 1-8 (2006).

Fusar-Poli, Laura et al., "Cannabinoids for People with Asd: A Systematic Review of Published and Ongoing Studies" Brain Sciences, vol. 10(572):1-18 (2020).

Extended European Search Report for corresponding EP22803457.5 dated Oct. 22, 2025, 5 pages.

(56)                    References Cited

OTHER PUBLICATIONS

Agarwal, Rumi et al., "Current state of evidence of cannabis utilization for treatment of autism spectrum disorders", BMC Psychiatry, vol. 19(328):1-10 (2019).

Protic, Dragana et al., "New Targeted Treatments for Fragile X Syndrome", Current Pediatric Reviews, vol. 15, pp. 251-258 (2019).

Thom, Robyn, P. et al., "Recent Updates in Psychopharmacology for the Core and Associated Symptoms of Autism Spectrum Disorder", Current Psychiatry Reports, vol. 23(79):1-9 (2021).

Yamasue, Hidenori et al., Emerging pharmacological therapies in fragile X syndrome and autism, Current Opinion, www.co-neurology.com, vol. 32(4):635-640 (2019).

Fleury-Teixeiran P, et al., "Effects of CBD-Enriched Cannabis Sativa Extract on Autism Spectrum Disorder Symptoms: An Observational Study of 18 Participants Undergoing Compassionate Use", Front. Neurol., vol. 10 (2019) https://doi.org/10.3389/fneur.2019.01145.

Clinical Study Of caNNabidiol in childrEn and adolesCenTs With Fragile X (Connect-Fx) (Connect-Fx), clinical trial NCT03614663 (version 14), retrieved from the Internet: URL: <https://clinicaltrials.gov/study/NCT03614663?tab=history&a=14#version-content-panel>[retrieved on Jan. 21, 2026], Feb. 3, 2020 (Feb. 3, 2020).

\* cited by examiner

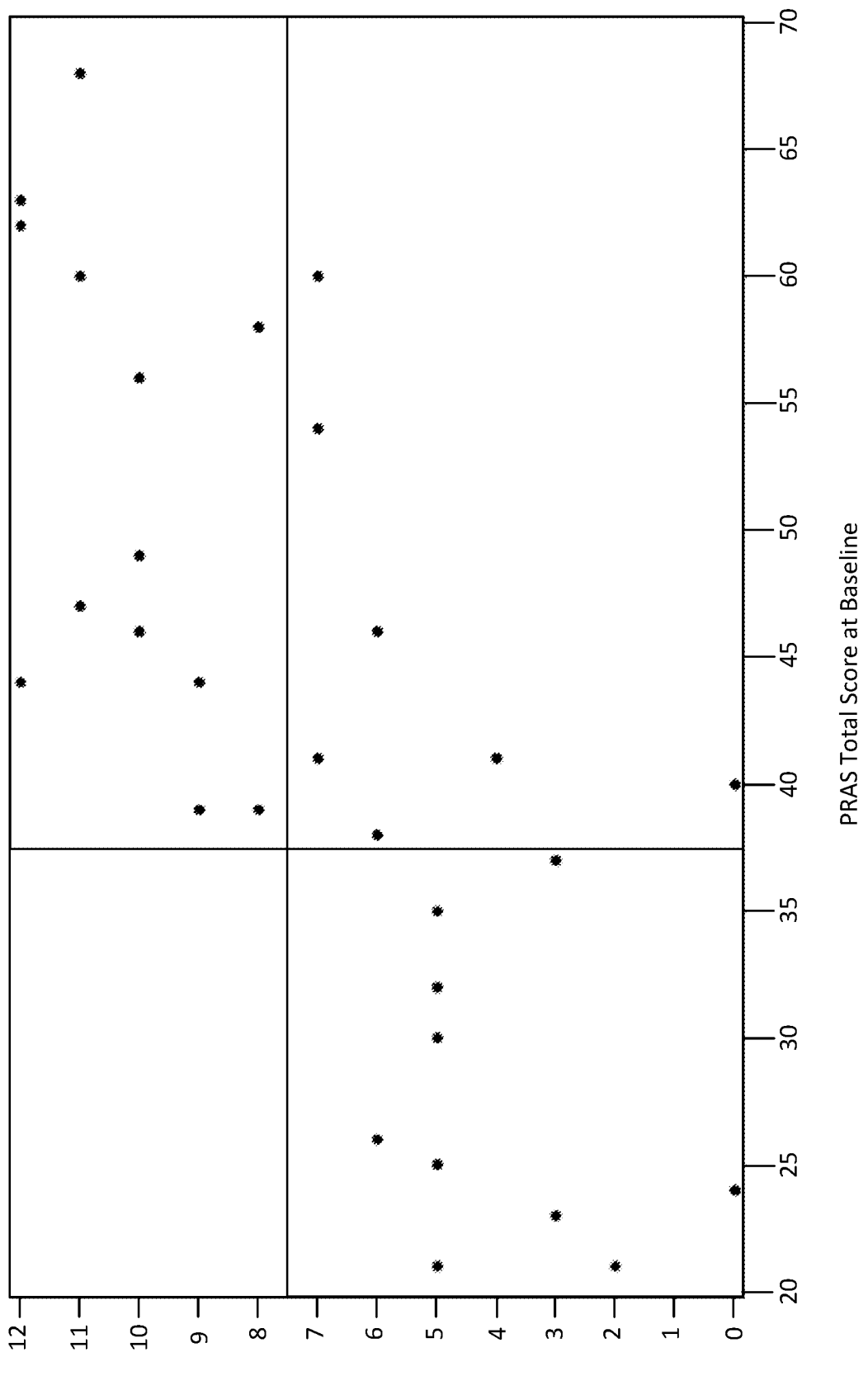

TREATMENT OF FRAGILE X SYNDROME WITH CANNABIDIOL

CROSS REFERENCE TO RELATED APPLICATIONS

This application claims the benefit of and priority to U.S. provisional application No. 63/271,015 filed Oct. 22, 2021. This application is also a continuation-in-part of U.S. patent application Ser. No. 17/465,141 filed Sep. 2, 2021, which is a continuation of U.S. patent application Ser. No. 16/737, 326 filed on Jan. 8, 2020, which is a continuation of U.S. patent application Ser. No. 16/411,248 filed on May 14, 2019, now U.S. Pat. No. 10,568,848, which is a continuation of U.S. patent application Ser. No. 16/220,249 filed on Dec. 14, 2018, now U.S. Pat. No. 10,314,792, which is a continuation of U.S. patent application Ser. No. 16/144,632 filed on Sep. 27, 2018, now U.S. Pat. No. 10,213,390, which claims the benefit of and priority to U.S. provisional application No. 62/564,834 filed Sep. 28, 2017 and U.S. provisional application No. 62/632,532 filed Feb. 20, 2018. The contents of each of which are hereby incorporated herein in their entirety.

FIELD OF THE TECHNOLOGY

The present disclosure relates to methods of treating one or more behavioral symptoms of Fragile X Syndrome in a subject by transdermally administering an effective amount of cannabidiol (CBD) to the subject wherein one or more behavioral symptoms of Fragile X Syndrome are treated in the subject.

BACKGROUND

Cannabinoids are a class of chemical compounds found in the *Cannabis* plant. The two primary cannabinoids contained in *Cannabis* are cannabidiol, or CBD, and Δ9-tetrahydrocannabinol, or THC. CBD lacks the psychoactive effects of THC. Studies have shown that CBD can be used to treat disorders such as epilepsy, arthritis, and cancer.

FXS is the most common inherited intellectual disability in males and a significant cause of intellectual disability in females. It is caused by a mutation in the Fragile X Mental Retardation 1 (FMR1) gene located on the X chromosome and leads to dysregulation of the endocannabinoid system including reductions in endogenous cannabinoids (2-AG and anandamide [AEA]). The disorder negatively affects synaptic function, plasticity and neuronal connections, and results in a spectrum of intellectual disabilities, social anxiety, and memory problems. In the US, there are about 71,000 patients suffering with FXS.

"Behavior problems are often the most significant concern reported by parents, and high levels of stress and depression and low levels of quality of life for parents are commonly associated with elevated problem behaviors in children." Wheeler A, Raspa M, Bann C, Bishop E, Hassl D, Sacco H, Bailey D B. 2014. *Anxiety attention problems, hyperactivity, and the Aberrant Behavior Checklist in fragile X syndrome. Am J Med Genet Part A* 164A:141-155, 141. "As a result, reduction in behavior problems is a primary focus of ongoing clinical trials testing the efficacy of new medications for FXS." Wheeler at pages 141-142.

The Anxiety, Depression, and Mood Scale (ADAMS) is an instrument that is used by clinicians, doctors, and researchers to assess the level of anxiety, depression and mood in patients with intellectual disabilities, including FXS. ADAMS consists of questions grouped into five subscales, including (i) general anxiety, (ii) social avoidance, (iii) compulsive behavior, (iv) manic/hyperactive behavior, and (v) depressed mood. Each question is answered by a clinician/doctor on a four-point scale ranging from 0 ("not a problem") to 3 ("severe problem"). In addition to subscale scores, the ADAMS yields a total score.

The original Aberrant Behavior Checklist (ABC) was "designed to assess behavioral concerns of adults within institutional settings." Wheeler at page 142. Since then, the original ABC has been adapted to address patients who are not institutionalized and specifically to address FXS. Id. The Aberrant Behavior Checklist—FXS Specific (ABC-FXS) scale is used by clinicians, doctors, and researchers to access certain behaviors in patients with FXS. The ABC-FXS scale has six subscales including (i) irritability, (ii) hyperactivity, (iii) socially unresponsive/lethargic, (iv) social avoidance, (v) stereotypy, and (vi) in appropriate speech. Similar to ADAMS, the ABC-FXS scale is a four-point Likert-type scale ranging from 0 (not a problem) to 3 (problem is severe).

SUMMARY

The present disclosure relates to a method of treating one or more behavioral symptoms of Fragile X Syndrome in a subject. The method includes transdermally administering an effective amount of cannabidiol (CBD) to the subject wherein one or more behavioral symptoms of Fragile X Syndrome are treated in the subject.

In some embodiments, the CBD is (−)-CBD. The effective amount of CBD can be between about 50 mg to about 500 mg daily. In some embodiments, the effective amount of CBD is initiated at about 50 mg daily and titrated up to about 500 mg daily. The effective amount of CBD can be initiated at about 50 mg daily and titrated up to about 250 mg daily. In some embodiments, the effective amount of CBD is initiated at 250 mg daily. The effective amount of CBD can be initiated at 500 mg daily. In some embodiments, the 500 mg daily dose is administered to patients that weigh greater than 35 kg. The CBD can be administered in a single daily dose or in two daily doses. In some embodiments, the effective amount of CBD can be 390 mg in divided daily doses.

The CBD can be formulated as a gel or an oil. In some embodiments, the CBD is formulated as a permeation-enhanced gel. The gel can contain between 1% (wt/wt) CBD to 7.5% (wt/wt) CBD. In some embodiments, the gel contains 4.2% (wt/wt) CBD. In some embodiments, the gel contains 7.5% (wt/wt) CBD.

In some embodiments, the transdermal preparation can be a cream, a salve or an ointment. The CBD can be delivered by a bandage, pad or patch.

Alleviating one or more behavioral symptoms of Fragile X Syndrome can include an improvement in a total score of an Anxiety, Depression and Mood Scale (ADAMS). In some embodiments, alleviating one or more behavioral symptoms of FXS can include improvement in one or more subscales of ADAMS. Alleviating one or more behavioral symptoms of Fragile X Syndrome can include improvement in one or more measures of an Aberrant Behavior Checklist for Fragile X (ABC-FXS).

In some embodiments, the one or more behavioral symptoms is selected from the group consisting of general anxiety, social avoidance, compulsive behavior, manic/hyperactive behavior, irritability, lethargy, stereotypy, and inappropriate speech. The behavioral symptom that is alleviated can be any one of general anxiety, social avoidance, compulsive behavior, manic/hyperactive behavior, irritability, lethargy, stereotypy, inappropriate speech, emotional functioning, psychosocial health, written communication, socialization, play and leisure, coping skills, internalizing behavior, externalizing behavior, tantrum/mood liability, hyperactivity/impulsivity, quality of life, or any combination thereof. In some embodiments, a single symptom is alleviated. In some embodiment, two, three, four, five, six, seven, eight, or nine symptoms are alleviated.

The CBD can be administered transdermally on the subject's upper arm and shoulder. In some embodiments, the CBD is administered transdermally on the subject's thigh or back.

The CBD can be synthetic CBD. The CBD can be purified CBD. The CBD can be botanically derived.

Transdermally administering an effective amount of cannabidiol (CBD) can reduce an intensity of at least one adverse event or side effect relative to orally administering CBD. The at least one adverse event or side effect can be a gastrointestinal (GI) adverse event. The at least one adverse event or side effect can be liver function. In some embodiments, the at least one adverse event is somnolence. In some embodiments, the frequency and intensity of somnolence is reduced as an adverse event.

In another aspect, a method is provided to treat one or more behavioral symptoms of an autism spectrum disorder (ASD) in a subject by transdermally administering an effective amount of CBD to the subject wherein the one or more behavioral symptoms of ASD are treated in the subject.

ASD is a behavioral diagnosis having a range of symptoms that are generally characterized by an impaired ability to communicate and interact socially with other people.

The one or more behavioral symptoms of ASD that can be treated include, for example, social avoidance, general anxiety, hyperactivity, depressed mood and compulsive behavior. Alleviating one or more behavioral symptoms of ASD can include an improvement in a total score of an Anxiety, Depression and Mood Scale (ADAMS). In some embodiments, alleviating one or more behavioral symptoms of ASD can include improvement in one or more subscales of ADAMS.

In some embodiments, the CBD is (–)-CBD. The effective amount of CBD can be between about 50 mg to about 500 mg daily. In some embodiments, the effective amount of CBD is initiated at about 50 mg daily and titrated up to about 500 mg daily. The effective amount of CBD can be initiated at about 50 mg daily and titrated up to about 250 mg daily. In some embodiments, the effective amount of CBD is initiated at 250 mg daily. The effective amount of CBD can be initiated at 500 mg daily. In some embodiments, the 500 mg daily dose is administered to patients that weigh greater than 35 kg. The CBD can be administered in a single daily dose or in two daily doses. In some embodiments, the effective amount of CBD can be 390 mg in divided daily doses.

The CBD can be formulated as a gel or an oil. In some embodiments, the CBD is formulated as a permeation-enhanced gel. The gel can contain between 1% (wt/wt) CBD to 7.5% (wt/wt) CBD. In some embodiments, the gel contains 4.2% (wt/wt) CBD. In some embodiments, the gel contains 7.5% (wt/wt) CBD.

In some embodiments, the transdermal preparation can be a cream, a salve or an ointment. The CBD can be delivered by a bandage, pad or patch.

Alleviating one or more behavioral symptoms of ASD can include an improvement in a total score of an Anxiety, Depression and Mood Scale (ADAMS). In some embodiments, alleviating one or more behavioral symptoms of ASD can include improvement in one or more subscales of ADAMS.

In some embodiments, the one or more behavioral symptoms is selected from the group consisting of general anxiety, social avoidance, compulsive behavior, manic/hyperactive behavior. The behavioral symptom that is alleviated can be any one of general anxiety, social avoidance, compulsive behavior, manic/hyperactive behavior, or any combination thereof. In some embodiments, a single symptom is alleviated. In some embodiment, two, three, or four behavioral symptoms are alleviated.

The CBD can be administered transdermally on the subject's upper arm and shoulder. In some embodiments, the CBD is administered transdermally on the subject's thigh or back.

The CBD can be synthetic CBD. The CBD can be purified CBD. The CBD can be botanically derived.

Transdermally administering an effective amount of cannabidiol (CBD) can reduce an intensity of at least one adverse event or side effect relative to orally administering CBD. The at least one adverse event or side effect can be a gastrointestinal (GI) adverse event. The at least one adverse even or side effect can be a liver function adverse event. In some embodiments, the at least one adverse event is somnolence. In some embodiments, the frequency and intensity of somnolence is reduced as an adverse event.

Handling behavior problems in subjects diagnosed with moderate to severe ASD can be challenging for caregivers. One such problem behavior is high irritability. High irritability can present as anger, frustration, distress, and meltdowns. Frequent episodes of high irritability can lead to considerable challenges for caregivers.

Unexpectedly, it has been found that response to CBD treatment of irritability in patients diagnosed with moderate to severe ASD is enhanced in subjects that also exhibit high social avoidance scores and/or high anxiety scores, relative to the general population of ASD subjects and Fragile X Syndrome (FSX) subjects who have symptoms of ASD. Specifically, about twice as many subjects that exhibit high social avoidance scores, high anxiety scores, or both, relative to the general population of ASD subjects, showed an improvement in irritability compared to subjects that had lesser avoidance and anxiety scores. These results show that the use of CBD for the treatment of irritability in ASD subjects is particularly effective in the subsets of these subjects that also exhibit high anxiety and/or high social avoidance.

In an embodiment, irritability in a subject diagnosed with autism spectrum disorder (ASD) may be treated by administering an effective amount of cannabidiol (CBD) to the subject. The administration of CBD improves the irritability of the subject, based on an ABC-C Irritability score. In an embodiment, the subject, before treatment, has an ABC-C irritability score greater than or equal to 12.

In another embodiment, the subject diagnosed with ASD, along with relatively high irritability, may exhibit relatively high social avoidance and/or relatively high anxiety. A subject diagnosed with moderate to severe ASD, in some embodiments, has an Autism Diagnostic Observation Schedule®, $2^{nd}$ Edition (ADOS-2) comparison score of greater than or equal to 3. In some embodiments, a subject having relatively high social avoidance has an ABC-C social avoidance score of greater than 5. In some embodiments, a subject having relatively high anxiety has a Parent Rated Anxiety Scale for ASD (PRAS-ASD) score of greater than 25.

In an embodiment, the CBD is synthetic CBD. Alternatively, the CBD may be botanically derived CBD that is unpurified or purified. The CBD may be administered orally or transdermally. In an embodiment, botanically obtained CBD does not contain THC. The effective amount of CBD may be 250 mg/day; 500 mg/day; or 750 mg/day. In some embodiments, an effective amount of CBD may be administered once/day or twice/day.

In some embodiments, the subject is diagnosed with Fragile X Syndrome (FXS), comorbid with ASD.

BRIEF DESCRIPTION OF THE DRAWINGS

Advantages of the present invention will become apparent to those skilled in the art with the benefit of the following detailed description of embodiments and upon reference to the accompanying drawings in which:

FIG. 1 is a plot of PRAS Total Score (Baseline) vs. ABC-C Social Avoidance subscale (Baseline).

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION

As used herein, the term "treating" or "treatment" refers to mitigating, improving, relieving, or alleviating at least one symptom (such as a behavioral symptom) of a condition, disease or disorder in a subject, such as a human, or the improvement of an ascertainable measurement associated with a condition, disease or disorder.

As used herein, the term "clinical efficacy" refers to the ability to produce a desired effect in humans as shown through a Food and Drug Administration (FDA), or any foreign counterparts, clinical trial.

As used herein, the term "cannabidiol" or "CBD" refers to cannabidiol; cannabidiol prodrugs; pharmaceutically acceptable derivatives of cannabidiol, including pharmaceutically acceptable salts of cannabidiol, cannabidiol prodrugs, and cannabidiol derivatives. CBD includes, 2-[3-methyl-6-(1-methylethenyl)-2-cyclohexen-1-yl]-5-pentyl-1,3-benzenediol as well as to pharmaceutically acceptable salts, solvates, metabolites (e.g., cutaneous metabolites), and metabolic precursors thereof. The synthesis of CBD is described, for example, in Petilka et al., *Helv. Chico. Acta,* 52:1102 (1969) and in Mechoulam et al., *J. Am. Chem. Soc.,* 87:3273 (1965), which are hereby incorporated by reference.

As used herein, the term "transdermally administering" refers to contacting the CBD with the patient's or subject's skin under conditions effective for the CBD to penetrate the skin.

Fragile X Syndrome (FXS) is a genetic condition that causes intellectual disability, behavioral and learning challenges and various physical characteristics. FXS affects 1 in 4,000 males and 1 in 8,000 females. Patients with FXS can exhibit one or more characteristics of ASD.

The present disclosure relates to a method of treating one or more behavioral symptoms of Fragile X Syndrome in a subject by transdermally administering an effective amount of cannabidiol (CBD) to the subject wherein one or more behavioral symptoms of Fragile X Syndrome are treated in the subject.

Clinical and preclinical data support the potential for CBD in treating epilepsy, arthritis, cancer, and Fragile X Syndrome. Therapeutic medicines have been developed that utilize innovative transdermal technologies to allow for sustained and controlled delivery of therapeutic levels of CBD. Transdermal delivery of cannabinoids (e.g., CBD) has benefits over oral dosing because it allows the drug to be absorbed through the skin directly into the bloodstream. This avoids first-pass liver metabolism, potentially enabling lower dosage levels of active pharmaceutical ingredients with a higher bioavailability and improved safety profile. Transdermal delivery also avoids the gastrointestinal tract, lessening the opportunity for GI related adverse events and the potential degradation of CBD by gastric acid into THC, which can be associated with unwanted psychoactive effects. Moreover, transdermal delivery of CBD reduces the intensity and frequency of somnolence adverse events, which are typically present in oral dosing of CBD. Transdermal delivery of CBD can avoid liver function adverse events, which are typically present in oral dosing of CBD. In some embodiments, transdermally administering an effective amount of CBD reduces an intensity of at least one adverse event by about 15% to about 95% relative to orally administering CBD.

The CBD can be in a gel form and can be pharmaceutically-produced as a clear, permeation-enhanced gel that is designed to provide controlled drug delivery transdermally with once- or twice-daily dosing. The CBD gel can between 1% (wt/wt) CBD to 7.5% (wt/wt) CBD. The CBD gel can have, for example, 4.2% (wt/wt) CBD or 7.5% (wt/wt) CBD). The CBD gel can be applied topically by the patient or caregiver to the patient's upper arm and shoulder, back, thigh, or any combination thereof.

The CBD gel can include diluents and carriers as well as other conventional excipients, such as wetting agents, preservatives, and suspending and dispersing agents.

The CBD gel can include a solubilizing agent, a permeation enhancer, a solubilizer, antioxidant, bulking agent, thickening agent, and/or a pH modifier. The composition of the CBD gel can be, for example, a. cannabidiol present in an amount of about 0.1% to about 20% (wt/wt) of the composition; b. a lower alcohol having between 1 and 6 carbon atoms present in an amount of about 15% to about 95% (wt/wt) of the composition; c. a first penetration enhancer present in an amount of about 0.1% to about 20% (wt/wt) of the composition; and d. water in a quantity sufficient for the composition to total 100% (wt/wt). Other formulations of the CBD gel can be found in International Publication No. WO 2010/127033, the entire contents of which are incorporated herein by reference.

Autism Spectrum Disorder (ASD) is a developmental disorder that affects communication and behavior in approximately one million pediatric and adolescent patients between the ages of five and 17 in the U.S. ASD refers to a range of conditions characterized by anxiety, repetitive patterns of behavior, impairments in social communication including verbal and non-verbal communication, and deficits in developing and maintaining relationships. Although autism can be diagnosed at any age, it is said to be a "developmental disorder" because symptoms generally appear in the first two years of life. Research suggests that genes can act together with influences from the environment to affect development in ways that lead to ASD. Newer studies suggest that ASD is linked to disruption in the endocannabinoid system.

The severity of symptoms of ASD in a subject is typically performed by looking at a. person's behavior and development. A number of behavioral tests have been developed to help clinicians measure the severity of behavioral symptoms of ASD. Exemplary tests to help clinicians determine the severity of symptoms of ASD include, but are not limited to, the following tests: Anxiety, Depression, and Mood Scale (ADAMS), Aberrant Behavior Checklist (ABC); Aberrant Behavior Checklist-Community (ABC-C); Diagnostic and Statistical Manual of Mental Disorders, Fifth Edition (DSM-5), Diagnostic and Statistical Manual of Mental Disorders, Fifth Edition, Text Revisions (DSM-5-TR); and Autism Diagnosis Observation Schedule-Second Edition (ADOS-2)

The Anxiety, Depression, and Mood Scale (ADAMS) is a behavioral test that is used by clinicians, doctors, and researchers to assess the level of anxiety, depression and mood in patients with intellectual disabilities, including ASD. The ADAMS test consists of questions grouped into five subscales, including (i) general anxiety, (ii) social avoidance, (iii) compulsive behavior, (iv) manic/hyperactive behavior, and (v) depressed mood. Each question is answered by a clinician/doctor on a four-point scale ranging from 0 ("not a problem") to 3 ("severe problem"). In addition to subscale scores, the ADAMS yields a total score.

Another test that can be used by clinicians to measure the severity of symptoms of ASD is the Aberrant Behavior Checklist-Community test (ABC-C). The original Aberrant Behavior Checklist (ABC) was designed to assess behavioral concerns of adults within institutional settings. The original ABC was later adapted to address patients who are not institutionalized and specifically to address subjects diagnosed with ASD. The Aberrant Behavior Checklist-Community (ABC-C) is used by clinicians, doctors, and researchers to access certain behaviors in non-institutionalized patients with ASD. The original ABC-C test has five subscales which include: (i) irritability, (ii) hyperactivity, (iii) social withdrawal, (iv) stereotypical behavior, and (v) inappropriate speech. Similar to ADAMS, the ABC-C scale is a four-point Likert-type scale ranging from 0 (not a problem) to 3 (problem is severe). The ABC-C irritability subscale was used as the basis for approval for the two atypical antipsychotics indicated for ASD. A modified score of the ABC-C was created to better assess behaviors in subjects diagnosed with FXS (ABC-C$_{FXS}$) which uses the same questions, but breaks the scoring into six subscales with the addition of a subscale for social avoidance.

The present disclosure also relates to a method of treating irritability symptoms of Autism Spectrum Disorder (ASD) in a subject by administering an effective amount of cannabidiol (CBD) to the subject wherein irritability symptoms of ASD are treated in the subject. The method includes transdermally administering an effective amount of cannabidiol (CBD) to the subject.

In an embodiment, the method can be used to treat irritability in a subject having moderate to severe ASD. A subject having moderate to severe ASD has an Autism Diagnostic Observation Schedule®, 2$^{nd}$ Edition (ADOS-2) comparison score of greater than or equal to 3.

Generally, a subject experiencing "high irritability" will experience irritability that is greater than a mean irritability of the relevant general population. Irritability can be determined using a scale such as the ABC-C Irritability subscale. A subject that is in need of treatment for high irritability has a high ABC-C Irritability score. As used herein, the term "high ABC-C Irritability score" refers to an ABC-C Irritability score of greater than 12, greater than 13, greater than 14, greater than 15, greater than 16, greater than 17, greater than 18, greater than 19 or greater than 20.

Generally, a subject experiencing "high social avoidance" will experience social avoidance that is greater than a mean social avoidance of the relevant general population. Social Avoidance can be determined using a scale such as the ABC-C$_{FXS}$ Social Avoidance subscale. A subject that has "high" social avoidance has an ABC-C$_{FXS}$ Social Avoidance score of greater than 5, greater than 6, greater than 7, greater than 8, or greater than 9.

Generally, a subject experiencing "high anxiety" will experience anxiety that is greater than a mean anxiety of the relevant general population. Anxiety can be determined using a scale such as the Parent Rated Anxiety Scale for ASD (PRAS-ASD). A subject that has "high" anxiety has a PRAS-ASD score of greater than 25, greater than 30, greater than 35, greater than 37, greater than 40, or greater than 45.

It should be understood that scores used to determine the high irritability, high anxiety, and high social avoidance are used to show an association with statistical data and clinical evaluation by physicians. A stated score associated with higher than usual behavior (e.g., high irritability, high social avoidance, and high anxiety) is a population estimate from studies that show that the clinical evaluation of such behaviors is associated with these scores, however, it is not necessarily an absolute threshold. Therefore, it should be understood that a physician does not necessarily rely on specific scores related to irritability, social avoidance, and anxiety to determine that a patient would benefit from pharmaceutical treatment. Rather use of a clinical evaluation, with or without determining specific scores associated with the behavior, may lead a physician to conclude that a subject is experiencing high irritability, high social avoidance, and high anxiety.

Therapeutic medicines have been developed that utilize innovative transdermal technologies to allow for sustained and controlled delivery of therapeutic levels of CBD. Transdermal cannabidiol delivery systems are taught in U.S. Pat. Nos. 8,449,908 and 8,435,556, both of which are incorporated herein by reference.

Transdermal delivery of cannabinoids (e.g., CBD) has benefits over oral dosing because it allows the drug to be absorbed through the skin directly into the bloodstream. This avoids first-pass liver metabolism, potentially enabling lower dosage levels of active pharmaceutical ingredients with a higher bioavailability and improved safety profile. Transdermal delivery also avoids the gastrointestinal tract, lessening the opportunity for GI related adverse events and the potential degradation of CBD by gastric acid into THC, which can be associated with unwanted psychoactive effects. Moreover, transdermal delivery of CBD reduces the intensity and frequency of somnolence as an adverse event, which are typically present in oral dosing of CBD. Transdermal delivery of CBD can avoid liver function adverse events, which are typically present in oral dosing of CBD. In some embodiments, transdermally administering an effective amount of CBD reduces an intensity of at least one adverse event by about 15% to about 95% relative to orally administering CBD.

The effective amount of CBD can be between about 50 mg to about 1000 mg daily. In some embodiments, the effective amount of CBD is initiated at about 50 mg daily and titrated up to about 750 mg daily. The effective amount of CBD can be initiated at about 50 mg daily and titrated up to about 250 mg daily, 500 mg daily, 750 mg daily, or 1000 mg daily. In some embodiments, the effective amount of CBD is initiated at 250 mg daily. The effective amount of CBD can be initiated at 500 mg daily. The effective amount of CBD can be initiated at 750 mg daily. The effective amount of CBD can be initiated at 1000 mg daily. In some embodiments, a daily dose of about 250 mg is administered to patients that weigh less than, or equal to, 35 kg. In some embodiments, a daily dose of about 500 mg is administered to patients that weigh more than 30 kg and less than, or equal to, 50 kg. In some embodiments, a daily dose of about 750 mg is administered to patients that weigh more than 50 kg. CBD can be administered in a single daily dose or in two daily doses. In some embodiments, the effective amount of CBD can be 390 mg in divided daily doses.

The CBD can be in a gel form and can be pharmaceutically-produced as a clear, permeation-enhanced gel that is designed to provide controlled drug delivery transdermally with once- or twice-daily dosing. The CBD gel can between 1% (wt/wt) CBD to 7.5% (wt/wt) CBD. The CBD gel can have, for example, 4.2% (wt/wt) CBD or 7.5% (wt/wt) CBD). The CBD gel can be applied topically by the patient or caregiver to the patient's upper arm and shoulder, back, thigh, or any combination thereof.

The CBD gel can include diluents and carriers as well as other conventional excipients, such as wetting agents, preservatives, and suspending and dispersing agents.

The CBD gel can include a solubilizing agent, a permeation enhancer, a solubilizer, antioxidant, bulking agent, thickening agent, and/or a pH modifier. The composition of the CBD gel can be, for example, a. cannabidiol present in an amount of about 0.1% to about 20% (wt/wt) of the composition; b. a lower alcohol having between 1 and 6 carbon atoms present in an amount of about 15% to about 95% (wt/wt) of the composition; c. a first penetration enhancer present in an amount of about 0.1% to about 20% (wt/wt) of the composition; and d. water in a quantity sufficient for the composition to total 100% (wt/wt). Other formulations of the CBD gel can be found in International Publication No. WO 2010/127033, the entire contents of which are incorporated herein by reference.

In some embodiments, the transdermal preparation can be a cream, a salve or an ointment. The CBD can be delivered by a bandage, pad or patch. The CBD can be administered transdermally on the subject's upper arm and shoulder. In some embodiments, the CBD is administered transdermally on the subject's thigh or back. The CBD can be synthetic CBD. The CBD can be purified CBD. The CBD can be botanically derived.

In some embodiments, the CBD is administered in a pharmaceutically acceptable preparation that does not contain THC. In some embodiments, the CBD is administered without THC or any other extracts of *cannabis*. In some embodiments, the CBD is synthetic CBD. In some embodiments it an extract. In some embodiments, it is purified.

Alleviating irritability in a subject diagnosed with Autism Spectrum Disorder (ASD) can include an improvement in an ABC-C irritability score. Irritability can be measured using the ABC-C irritability subset score. High irritability in a subject may be indicated if the ABC-C irritability score is equal to or greater than 18. In an embodiment, an improvement in the ABC-C irritability score is indicated when the ABC-C irritability score of a subject is less than 18, or less than 17, or less than 16, or less than 15, or less than 14, or less then 13, or less then 12, or less than 11, or less than 10, or less than 9, or less then 8, or less than 7, or less than 6, or less than 5, or less than 4, or less than 3, or less than 2, or less than 1, or equal to 0, after treatment of the subject with CBD. In an embodiment, an improvement in the ABC-C irritability score is indicated when the ABC-C irritability score in a subject, after treatment with CBD, is reduced by at least 3, or reduced by at least 4, or reduced by at least 5, or reduced by at least 6, or reduced by at least 7, or reduced by at least 8, or reduced by at least 9, or reduced by at least 10, or reduced by at least 11, or reduced by at least 12, or reduced by at least 13, or reduced by at least 14, or reduced by at least 15, or reduced by at least 16, or reduced by at least 17, or reduced by at least 18. In an embodiment, an improvement in the ABC-C irritability score is indicated when the ABC-C irritability score in a subject, after treatment with CBD, is reduced by at least 5%, or reduced by at least 10%, or reduced by at least 15%, or reduced by at least 20%, or reduced by at least 25%, or reduced by at least 30%, or reduced by at least 35%, or reduced by at least 40%, or reduced by at least 45%, or reduced by at least 50%, or reduced by at least 55%, or reduced by at least 60%.

Alleviating irritability in a subject diagnosed with moderate to severe ASD can also include an improvement in a total score of an Anxiety, Depression and Mood Scale (ADAMS). In some embodiments, alleviating one or more behavioral symptoms of ASD can include improvement in one or more subscales of ADAMS.

In some embodiments, the subject is also being administered one or more additional medications. The one or more additional medications, in some embodiments, are selected from the group consisting of an anti-depressant, an anxiolytic, an alpha-2-adrenergic agonist, a psychostimulant, an antipsychotic medication, and combinations thereof.

In some embodiments, the one or more additional medications include an antipsychotic medication. Examples of antipsychotic medications typically administered to subjects diagnosed with ASD include, but are not limited to, risperidone, aripiprazole, haloperidol, olanzapine, ziprasidone, and quetiapine fumarate in some embodiments.

In some embodiments, the one or more additional medications include an alpha adrenergic agonist. Examples of alpha-2-adrenergic agonists typically administered to subjects diagnosed with ASD include, but are not limited to, clonidine and guanfacine.

In some embodiments, the one or more additional medications include an anti-depressant. For example, a selective serotonin reuptake inhibitor (SSRI) anti-depressant may be also be administered to a subject as an additional medication. Examples of SSRIs that are used in subjects with ASD include, but are not limited to, fluoxetine, citalopram, and escitalopram.

In some embodiments, the one or more psychotropic medications include a psychostimulant medication. Examples of psychostimulant medications typically administered to subjects diagnosed with ASD include, but are not limited to, methylphenidate HCl, atomoxetine HCl, dexamfetamine, and lisdexamfetamine mesilate.

Unexpectedly, it has been found that treatment of irritability in a subject diagnosed with ASD is enhanced if the patient has a high social avoidance score and/or a high anxiety score. Typically, the severity of symptoms in patients with ASD are determined using the ABC-C test. As discussed before, the ABC-C test has five subscales which include (i) irritability, (ii) hyperactivity, (iii) social withdrawal, (iv) stereotypical behavior, and (v) inappropriate speech. The ABC-C$_{FXS}$ test was created to better assess behaviors of subjects diagnosed with FXS. The ABC-C$_{FXS}$ test uses the same questions as the ABC-C test, but breaks the scoring into six subscales with the addition of a subscale for social avoidance. When the ABC-C$_{FXS}$ test is applied to subjects with ASD (but not a diagnosis of FXS), this unique application of the ABC-C$_{FXS}$ test provides a novel separation of subjects based on criteria previously not used to study subjects with ASD, (i.e., social avoidance). When applying the ABC-C$_{FXS}$ test to ASD subjects, it was found that a subject having an ABC-C$_{FXS}$ Social Avoidance score of greater than 7 showed twice as much improvement in irritability, compared to subjects having an ABC-C$_{FXS}$ social avoidance score of less than, or equal to 7. By modifying the existing testing standards for the severity of symptoms with patients diagnosed with ASD (ABC-C) with a standard that was developed for patients diagnosed with FXS (ABC-C$_{FXS}$), a preferential and positive response to treatment with CBD was discovered for irritability in subjects having high ABC-C$_{FXS}$ social avoidance scores.

It was also found that subjects having a Parent Rated Anxiety Scale (PRAS) score of greater than 37 showed twice as much improvement in irritability, compared to subjects having a PRAS score of less than, or equal to 37.

In some embodiment, the subject may be diagnosed with Fragile X Syndrome (FXS) comorbid with moderate to severe ASD. Similar to subjects that have a diagnosis of ASD, patients diagnosed with FXS and ASD show improved irritability when treated with CBD, particularly transdermal CBD. It was also found that FXS subjects having high social avoidance scores and/or high anxiety scores also show the same enhanced reduction in irritability as seen with ASD patients without FXS.

EXAMPLES

Example 1: Study Design and Data

A total of 20 patients (mean age=10.8, SD=4.0) were enrolled in a 12-week study. Eighteen patients (14 males, 4 females) aged 6 to 17 years of age (mean=11.2 SD=3.96) with Fragile X as confirmed by molecular documentation of FMR1 full mutation completed the open label FAB-C study through week 12. CBD gel was added on to other medications being administered. The first six weeks of the study were designed to titrate dosing in patients. Dosing was initiated at 50 mg CBD daily and could be increased to 250 mg CBD daily. Weeks 7 through 12 of the study comprised the maintenance period where patients were treated at the dose established by week six at a maximum of 250 mg CBD daily. At the completion of the study, patients could enter an open label extension study for up to 12 months.

The primary endpoint for the trial was the change in the total score of the Anxiety, Depression, and Mood Scale (ADAMS) from baseline to week 12. The ADAMS is a 28-item scale designed to assess general anxiety, social avoidance, compulsive behavior, manic/hyperactive behavior, and depressed mood. It has been validated in patients with FXS.

Results for the primary endpoint are summarized in Table 1, detailing efficacy scales mean (standard deviation) values at baseline and week 12 for the ADAMS Total Score.

TABLE 1

| | Baseline (n = 18) | Week 12 (n = 18) | Percent Change from Baseline (%; n = 18) | p Value* |
|---|---|---|---|---|
| ADAMS: Total Score | 32.1 (14.36) | 18.1 (8.32) | −43.61 | p < 0.0001 |

*P-values are presented for the comparison of the Week 12 value to the Baseline value for the total score and each subscale, among those who completed the study (n = 18).

The subscales of the ADAMS are summarized in Table 2, detailing efficacy scales mean (standard deviation) values at baseline and week 12.

TABLE 2

| | Baseline (n = 18) | Week 12 (n = 18) | Percent Change from Baseline (%; n = 18) | p Value* |
|---|---|---|---|---|
| ADAMS: Manic/ Hyperactive Behavior Subscale | 8.8 (3.99) | 6.1 (3.29) | −30.68 | p = 0.0003 |
| ADAMS: Depressed Mood Subscale | 2.9 (3.94) | 2.0 (2.35) | −31.03 | p = 0.1417 |
| ADAMS: Social Avoidance Subscale | 9.9 (5.18) | 4.8 (2.07) | −51.52 | p = 0.0002 |
| ADAMS: General Anxiety Subscale | 9.4 (4.35) | 4.6 (3.35) | −51.06 | p < 0.0001 |
| ADAMS: Compulsive Behavior Subscale | 2.7 (2.40) | 1.4 (1.42) | −48.15 | p = 0.0262 |

*P-values are presented for the comparison of the Week 12 value to the Baseline value for the total score and each subscale, among those who completed the study (n = 18).

Compared to the baseline total score, the CBD transdermal gel treated patients has a 44% reduction (p<0.0001) in the ADAMS Total Score. Furthermore, the CBD transdermal gel treated patients has statistically and clinically significant improvement compared to baseline in all but one of the ADAMS subscales (i.e., manic/hyperactive behavior, social avoidance, general anxiety, and compulsive behavior) at week 12. A significant change was not observed for the depressed mood subscale of the ADAMS.

Multiple secondary efficacy endpoints including the Aberrant Behavior Checklist-FXS Specific (ABC-FXS), the Pediatric Anxiety Rating Scale (PARS-R), Visual Analog Scale (VAS) for Anxiety, Hyperactivity and Tantrum/Mood Lability, the Vineland Adaptive Behavior (VLD) III, and the Pediatric Quality of Life (PedsQL™). Both the PARS-R and the Vineland scales are clinician-rated, while the other scales are caregiver-rated.

The primary and secondary endpoints were evaluated prior to and following 12 weeks of drug administration. The results of the secondary endpoints reinforce the results demonstrated in the ADAMS. Consistent with findings from the ADAMS, patients taking the CBD transdermal gel demonstrated statistically and clinically significant 12-week reductions in all subscales of the ABC-FXS (i.e., irritability, hyperactivity, socially unresponsive/lethargic, social avoidance, stereotypy, and inappropriate speech), and both total score calculations of the PARS-R (i.e., 5- and 7-item).

Patients also showed significant improvement between Baseline and Week 12 scores for all remaining scales except for the Physical Function, School Functioning, and Social Functioning subscales of the PedsQL, as well as some subscales of the VLD (e.g., communication, daily living skills). Both the VLD and ADAMS are being administered in the extension Phase 2 of the trial.

Results from the ABC-FXS are summarized in Table 3, detailing efficacy scales mean (standard deviation) values at baseline and week 12.

TABLE 3

| | Baseline (n = 18) | Week 12 (n = 18) | Percent Change from Baseline (%; n = 18) | p Value* |
|---|---|---|---|---|
| ABC: Irritability | 17.7 (12.68) | 10.6 (11.03) | −40.11 | p = 0.0096 |
| ABC: Hyperactivity | 13.7 (9.09) | 9.8 (7.38) | −28.47 | p = 0.0237 |
| ABC: Socially Unresponsive/ Lethargic | 9.2 (6.40) | 4.1 (4.09) | −55.43 | p = 0.0034 |
| ABC: Social Avoidance | 5.1 (3.46) | 2.3 (2.22) | −54.90 | p = 0.0005 |
| ABC: Stereotypy | 8.1 (5.91) | 3.2 (3.07) | −60.49 | p = 0.0006 |
| ABC: Inappropriate Speech | 5.9 (2.30) | 3.5 (2.66) | −40.68 | p = 0.0018 |

*P-values are presented for the comparison of the Week 12 value to the Baseline, among those who completed the study (n = 18).

Results from the PARS-R are summarized in Table 4, detailing efficacy scales mean (standard deviation) values at baseline and week 12.

TABLE 4

| | Baseline (n = 18) | Week 12 (n = 18) | Percent Change from Baseline (%; n = 18) | p Value* |
|---|---|---|---|---|
| PARS-R - 5 Item | 15.7 (3.88) | 10.6 (3.43) | −32.48 | p = 0.0006 |
| PARS-R - 7 Item | 21.3 (5.55) | 14.4 (4.54) | −32.39 | p = 0.0004 |

*P-values are presented for the comparison of the Week 12 value to the Baseline value, among those who completed the study (n = 18).

Results from the VAS for Anxiety, Hyperactivity and Tantrum/Mood Lability are summarized in Table 5.

TABLE 5

| | Baseline (n = 18) | Week 12 (n = 18) | Percent Change from Baseline (%; n = 18) | p Value* |
|---|---|---|---|---|
| VAS - Hyperactivity/ Impulsivity | 5.9 (2.43) | 3.6 (2.49) | −38.98 | p = 0.0002 |
| VAS - Tantrum/Mood Liability | 4.7 (2.09) | 3.2 (2.18) | −31.91 | p = 0.0023 |
| VAS - Anxiety | 6.0 (2.05) | 3.8 (1.93) | −36.67 | p = 0.0005 |

*P-values are presented for the comparison of the Week 12 value to the Baseline value, among those who completed the study (n = 18).

Results from the PedsQL are summarized in Table 6, detailing efficacy scales mean (standard deviation) values at baseline and week 12.

TABLE 6

| | Baseline (n = 18) | Week 12 (n = 18) | Percent Change from Baseline (%; n = 18) | p Value* |
|---|---|---|---|---|
| PedsQL: Total Score | 57.8 (18.78) | 67.7 (18.27) | 17.13 | p = 0.0100 |
| PedsQL: Physical Functioning | 67.9 (27.36) | 78.0 (22.39) | 14.87 | p = 0.0606 |

TABLE 6-continued

| | Baseline (n = 18) | Week 12 (n = 18) | Percent Change from Baseline (%; n = 18) | p Value* |
|---|---|---|---|---|
| PedsQL: Emotional Functioning | 64.0 (20.72) | 78.3 (16.63) | 22.34 | p = 0.0394 |
| PedsQL: Social Functioning | 37.3 (24.70) | 49.0 (24.35) | 31.37 | p = 0.0717 |
| PedsQL: School Functioning | 55.7 (19.17) | 59.1 (22.47) | 6.10 | p = 0.3580 |
| PedsQL: Psychosocial Health | 52.4 (17.22) | 62.2 (18.91) | 18.70 | p = 0.0408 |

*P-values are presented for the comparison of the Week 12 value to the Baseline value, among those who completed the study (n = 18).

Results from the VLD III are summarized in Table 7, detailing efficacy scales mean (standard deviation) values at baseline and week 12.

TABLE 7

| | Baseline (n = 18) | Week 12 (n = 18) | Percent Change from Baseline (%; n = 18) | p Value* |
|---|---|---|---|---|
| VLD III: Overall Adaptive Behavior Composite | 46.1 (16.29) | 48.9 (16.49) | 6.07 | p = 0.0472 |
| VLD III: Communication | 36.7 (18.52) | 39.2 (20.34) | 6.81 | p = 0.2968 |
| VLD III: Communication - Receptive | 3.9 (3.43) | 5.3 (4.34) | 35.90 | p = 0.0752 |
| VLD III: Communication - Expressive | 3.3 (3.63) | 3.7 (4.07) | 12.12 | p = 0.5070 |
| VLD III: Communication - Written | 4.4 (3.81) | 3.8 (3.64) | −13.64 | p = 0.0293 |
| VLD III: Daily Living Skills | 52.7 (21.19) | 54.6 (18.46) | 3.61 | p = 0.3911 |
| VLD III: Daily Living Skills - Personal | 5.7 (4.26) | 6.2 (4.33) | 8.77 | p = 0.3374 |
| VLD III: Daily Living Skills - Domestic | 9.6 (3.42) | 9.5 (3.09) | −1.04 | p = 0.9395 |
| VLD III: Daily Living Skills - Community | 4.6 (3.09) | 4.7 (2.93) | 2.17 | p = 0.5636 |
| VLD III: Socialization | 45.9 (16.22) | 50.9 (17.83) | 10.89 | p = 0.0344 |
| VLD III: Socialization - Interpersonal Relationships | 5.3 (3.51) | 5.9 (3.64) | 11.32 | p = 0.2937 |
| VLD III: Socialization - Play and Leisure | 3.4 (2.91) | 4.5 (3.93) | 32.35 | p = 0.0350 |
| VLD III: Socialization - Coping Skills | 6.6 (2.93) | 7.8 (2.84) | 18.18 | p = 0.0246 |
| VLD III: Maladaptive Behavior - Internalizing | 19.9 (1.71) | 18.7 (1.79) | −6.03 | p = 0.0486 |
| VLD III: Maladaptive Behavior - Externalizing | 18.7 (2.42) | 17.2 (2.66) | −8.02 | p = 0.0090 |

*P-values are presented for the comparison of the Week 12 value to the Baseline value, among those who completed the study (n = 18).

Among the 18 patients who completed 12 weeks of treatment, average improvement in overall anxiety and depression (ADAMS Total Score) reached 44% (p<0.01), with particular benefit observed for the General Anxiety (51%; p<0.01) and Compulsive Behavior subscales (48%; p<0.05). Additionally, improvements as measured by $ABC_{FXS}$ ranging from 28% (Hyperactivity subscale; p0<0.05) to 60% (Stereotypy subscale; p0<0.01) were observed in aberrant behavior, with the Social Avoidance (p<0.01) and Social Unresponsiveness/Lethargy subscales (p<0.01) each improving by 55% during the treatment period. Beyond individual symptoms, quality of life improved by 17% (p=0.01).

The trial successfully met its primary endpoint, achieving a 44% improvement (P<0.0001) in the total ADAMS score at week twelve compared to baseline. The trial also achieved clinically meaningful improvements in all measures of the ABC-FXS, which address the key symptoms of FXS including irritability, hyperactivity, social unresponsiveness, social avoidance, stereotypy, and inappropriate speech.

Following the 12-week open-label study, patients were allowed to roll into a 1-year open-label extension study. 72% (n=13) of the 18 patients who completed the initial 12-week study rolled into the extension. While the open-label extension is ongoing, some data have been collected through Week 38 (12 weeks in initial study and up to 6 months in the extension study). Results from the extension study demonstrate continued gains in the two measures collected (ADAMS and $ABC_{FXS}$). Indeed, those who have completed a Week 38 visit (n=4) showed significant gains from screening in overall anxiety and depression, with participants experiencing an average improvement in the ADAMS total score of 74%. Similar improvement was observed for aberrant behavior, ranging from 75% (Irritability subscale) to 96% (Social Avoidance subscale) and 97% (Socially Unresponsiveness/Lethargy subscale) at Week 38.

The open-label extension continues to be ongoing and data has been collected through Week 51. The results are summarized in Table 8 ($ABC_{FXS}$) and Table (ADAMS).

Example 2

TABLE 8

(ABC$_{FXS}$)

|  | Screening (baseline score) N = 12 | Week 12 Mean Change (%) N = 12 | Week 38 Mean Change (%) N = 9 | Week 51 Mean Change (%) N = 9 | Week 51 P values |
|---|---|---|---|---|---|
| Irritability | 22.3 | 51.1 | 63.7 | 59.2 | 0.0007 |
| Hyper-activity | 16.6 | 36.7 | 48.2 | 40.4 | 0.0037 |
| Socially Un-responsive/ Lethargic | 10.8 | 65.7 | 83.3 | 72.2 | 0.0035 |
| Social Avoidance | 5.7 | 57.9 | 75.4 | 77.2 | 0.0013 |
| Stereotypy | 9.7 | 60.8 | 73.2 | 64.9 | 0.0012 |
| Inappropri-ate Speech | 6.2 | 56.5 | 66.1 | 56.5 | <0.0001 |

TABLE 9

(ADAMS)

|  | Screening (baseline score) N = 12 | Week 12 Mean Change (%) N = 12 | Week 38 Mean Change (%) N = 12 | Week 51 Mean Change (%) N = 12 | Week 51 P values |
|---|---|---|---|---|---|
| Manic/ Hyper-activity | 8.8 | 34.1 | 53.4 | 45.5 | 0.0014 |
| Depressed Mood | 3.2 | 43.8 | 62.5 | 59.4 | 0.0032 |
| Social Avoidance | 9.9 | 52.5 | 61.6 | 55.6 | 0.0004 |
| General Anxiety | 9.8 | 55.1 | 58.2 | 58.2 | <0.0001 |
| Compulsive Behavior | 3.2 | 50.0 | 59.4 | 59.4 | 0.0213 |
| Total Score | 33.3 | 48.6 | 59.2 | 54.4 | <0.0001 |

CBD gel was well tolerated, with excellent skin tolerability. One patient discontinued due to worsening of pre-existing eczema. No other adverse events led to discontinuation and no adverse events were considered severe. The most common adverse events were mild-moderate gastro-enteritis (n=6) and upper respiratory tract infection (n=5). However, no patient experienced drug-related GI events during the 12-week treatment period and no THC was detected in the plasma.

The clinical results of the trial are significant for the many patients worldwide with FXS who currently have no approved therapeutic options to treat their symptoms. The data, in particular the improvements in anxiety, social avoidance, and irritability as measured by ADAMS, ABC-FXS and PARS-R, are significant. The CBD gel was very well tolerated in children and adolescents with FXS.

Example 2: Patient Monograph as Reported by Parent

This is the report regarding a 7 year old child participating in the above study and continuing on an extension study—as reported by the caregiver. The caregiver's son has full mutation Fragile X Syndrome. He is reported, prior to the trial, to be non-verbal, severely intellectually impaired, visually impaired, still in need of diapers and as having very severe GI issues requiring that he is fed by a feeding tube every two hours. Prior to the beginning the trial the child never ever made eye contact, rarely could leave his home without severe emotional distress, did not initiate any form of communication at all, intensely disliked being touched including by his parents, would not allow even family to sit next to him, and would leave the room if anyone walked into it.

Within the first two weeks of the trial, the patient began to make more eye contact, initiated physical contact with his family, e.g., grabbing his mother's hand, initiated emotional contact with his family including seeking to be in the same room with his family, and exhibited improved ability to leave the house, even to the extent the family could take their very first vacation together.

After the end of the initial trial and a few weeks into the extended trial, the caregiver recorded another big change in the patient. He started greeting his family, initiated and engaged in games that are more complex, exhibited/shared preferences for things instead of only rejecting all choices, and he began acknowledging the family pets. He also allowed his doctor to touch him and hold onto him without getting distressed. Patient began to use body signing (sign language) for the very first time. Patient communicated very clearly that he missed his mother for the very first time and was eager to be embraced and held by his mother.

Patient is reported to be happier, more relaxed, able to engage the world in ways he could not before, and able to learn new skills that he could not previously. His teachers, therapists and aids have also remarked in the changes in the patient.

Example 3: Treatment of ASD— BRIGHT Study

An exploratory open-label safety, tolerability and efficacy study of Zygel™ ZYN002 transdermal gel to 37 children and adolescents with autism spectrum disorder was conducted. The patient population (ages 4 through 17 years old) were predominantly moderate-to-severe ASD patients. ASD was confirmed by Diagnostic and Statistical Manual of Mental Disorders, 5th edition (DSM-5) diagnostic criteria to assess the safety and efficacy of ZYN002 in treating ASD-related behaviors as measured by a variety of efficacy assessments. These included the Aberrant Behavior Check-list-Community (ABC-C); the Autism Diagnostic Observation Schedule®, 2$^{nd}$ Edition (ADOS-2); and the Parent Rated Anxiety Scale-Autism Spectrum Disorder (PRAS-ASD). ZYN002 was administered to patients with moderate-to-severe symptoms of ASD as add-on therapy to their standard of care.

Patient Demographics.

The majority of the patients were male (92%) with a mean age of 9.2 years. Patients weighed between 15 and 108 kilograms (mean=41.6; median=30.2). The mean time to diagnosis in this population was 5.4 years. The majority of patients had moderate or severe ASD at baseline as measured by the ADOS®-2 comparison score (94%) and Diagnostic and Statistical Manual of Mental Disorders, 5th edition, severity levels (92%). The mean ABC-C Irritability score was 30.3, and 9 patients (24.3%) had PRAS-ASD scores indicative of possible clinical anxiety, further highlighting the severity of symptoms in the enrolled patient population.

The majority (92%) of patients entered the trial with the use of at least one underlying medication. 65% of patients were on at least one psychotropic medication, e.g., anti-depressants, anxiolytics, and antipsychotics. 14 of the 37 subjects were on antipsychotics, 11 on risperidone, 1 on haloperidol, 1 on olanzapine, and 1 on quetiapine fumarate. 16 were on psychostimulant agents used for ADHD and nootropics, including clonidine (6), guanfacine (5), methylphenidate HCl (7), atomoxetine HCl (2), dexamfetamine (1), and lisdexamfetamine mesilate (2).

Protocol

Subjects were administered a 250 or 500 mg total daily dose, administered twice daily, of CBD in the form of ZYN002 CBD transdermal gel for 14 weeks. After completing dosing in the 14-week period, participants who qualified were given the option to enroll in a six-month extension trial. The trial evaluated multiple efficacy assessments, including the ABC-C, PRAS-ASD, Autism Parenting Stress Index, Autism Impact Measure (AIM), and Clinical Global Impression-Severity (CGI-S) and Improvement (CGI-I). The ABC-C irritability subscale was used as the basis for approval for the two atypical antipsychotics indicated for ASD (risperidone and aripiprazole).

Results

All five subscales of the ABC-C as well as the Parent Rated Anxiety Scale-Autism Spectrum Disorder (PRAS-ASD) showed both statistically significant and clinically meaningful improvements at 14 weeks of treatment versus baseline.

Table 1 summarizes the 14-week improvement from each of the subscales of the ABC-C. All results were statistically significant; p<0.001 for all subscales.

TABLE 1

| ABC-C Improvement at 14 Weeks | | | |
| --- | --- | --- | --- |
| | Baseline (n = 36) | Week 14 (n = 28) | Mean % improvement |
| ABC: Irritability | 30.3 | 18.2 | 39.1% |
| ABC: Inappropriate Speech | 7.4 | 5.2 | 42.5% |
| ABC: Stereotypy | 12.3 | 7.9 | 39.1% |
| ABC: Social withdrawal | 25.1 | 16.5 | 36.4% |
| ABC: Hyperactivity | 37.0 | 23.9 | 35.6% |

There was a 40% improvement in stereotypic behavior on the ABC scale, a 33% improvement in repetitive behavior on Parent Reported Anxiety Scale, and an unexpected overall improvement in children with this severity of ASD and who were also on antipsychotic medications. The results are both statistically significant and clinically meaningful.

The results of other efficacy assessments reinforce the results demonstrated in the ABC-C. For example, patients on ZYN002 experienced a mean improvement of 46% at week 14 from a baseline score of 40.8 as measured by the PRAS-ASD (p<0.001) and 57% of patients were assessed as very much or much improved at week 14 as measured by the Clinical Global Impressions-Improvement scale (CGI-I).

ZYN002 was well tolerated in this trial with no serious adverse events (SAE) reported. Twenty-eight patients completed the 14-week trial; this discontinuation rate is consistent with other trials in ASD. Only one patient was lost to follow up with no post-treatment efficacy evaluation. Less than half (49%) of the patients experienced any adverse event (non-related or related to study drug), all of which were mild (75%) or moderate (25%). Only 14% of patients experienced an adverse event deemed to be treatment-related, all of which were application site-related and most were mild and transient. There were no severe adverse events reported during the study. Eighteen (18) patients who completed the BRIGHT trial enrolled in the open label extension.

Results

All five subscales of the ABC-C as well as the Parent Rated Anxiety Scale-Autism Spectrum Disorder (PRAS-ASD) showed both statistically significant and clinically meaningful improvements at 14 weeks of treatment versus baseline. Table 1 summarizes the week 6 and week 14 ABC-C results.

Example 4: Treatment of Irritability in Subjects

In data obtained from the previously described trials, it was noted that administration of transdermal CBD had a significant improvement in the irritability score of subjects diagnosed with moderate to severe ASD. A summary of the results for the completers (N=28) from the study for the open-label safety, tolerability and efficacy study of Zygel™ ZYN002 transdermal gel (See Example 1) are presented in Table 1.

The data collected from the studies presented herein, and other similar studies were pooled together and analyzed. Table 2 presents a summary of pooled data collected from 156 subjects. The subjects had a baseline ABC-C Irritability score of greater than, or equal to, 18. The subjects had moderate to severe symptoms of ASD (ADOS-2, comparison score greater than, or equal to, 5). The data presented in Table 2 is the Week 12 change in ABC-C Irritability of all patients. In previous studies (such as presented in Example 1, Table 1) the data was enriched by removing the non-completers from the analysis and only presenting data from the completers. The current analysis in Table 2 shows that, without data enrichment, Zygel™ ZYN002 transdermal gel provided a minimal improvement, compared to placebo, of ABC-C Irritability in patients with FXS and comorbid ASD.

TABLE 2

| Parameter Time Point Statistic | Placebo (N = 73) | ZYN002 (N = 83) | Total (N = 156) |
| --- | --- | --- | --- |
| N | 73 | 80 | 153 |
| Mean | −2.89 | −4.80 | −3.89 |
| SD (SE) | 7.17 (0.84) | 7.09 (0.79) | 7.17 (0.58) |
| Median | −2.0 | −5.0 | −3.0 |
| Min, Max | −23, 17 | −31, 10 | −31, 17 |

The data presented in Table 2 was further analyzed by limiting the data to subjects that had a baseline ABC-C Irritability score of greater than, or equal to, 18 and an ABC-C$_{FXS}$ Social Avoidance score of greater than 7. These results were compared to patents that had a baseline ABC-C Irritability score of greater than, or equal to, 18 and an ABC-C$_{FXS}$ Social Avoidance score of less than, or equal to 7. The results of this analysis are presented in Table 3. This data shows that subjects having an ABC-C$_{FXS}$ Social Avoidance score of greater than 7 had a much better response to transdermal CBD administration than subjects having an ABC-C$_{FXS}$ Social Avoidance score of less than, or equal to 7.

TABLE 3

| | Parameter Time Point Statistic | Placebo | ZYN002 |
|---|---|---|---|
| SA >7 | N | 29 | 27 |
| | Mean | −3.34 | −7.96 |
| | SD (SE) | 7.66 (1.42) | 9.46 (1.82) |
| | Median | 0.0 | −6.0 |
| | Min, Max | −25, 4 | −31, 10 |
| SA ≤7 | N | 23 | 35 |
| | Mean | −5.57 | −4.74 |
| | SD (SE) | 6.8 (1.42) | 6.03 (1.02) |
| | Median | −5.0 | −4.0 |
| | Min, Max | −23, 6 | −17, 6 |

Further, data from the BRIGHT study in ASD, showed that baseline anxiety scores on the Parent Rated Anxiety Scale for ASD (PRAS-ASD) were found to be correlated with ABC-C$_{FXS}$ Social Avoidance. FIG. 1 shows a plot of PRAS Total Score (Baseline) vs. ABC-C$_{FXS}$ Social Avoidance subscale (Baseline). The data shows correlation between social avoidance and anxiety, with a correlation coefficient of 0.45526 (P value=0.005).

This led to further analysis of the Zygel™ ZYN002 transdermal gel data to see the effect of Zygel on ABC-C Irritability score in subjects having high PRAS-ASD anxiety scores (greater than 37). This analysis, presented in Table 4, shows that subjects with baseline ABC-C Irritability score of greater than, or equal to, 18 and PRAS-ASD scores greater than 37 showed better improvement of irritability compared to subjects with a PRAS-ASD score less than, or equal to, 37. The improvement in irritability in subjects with high PRAS-ASD scores is summarized in Table 4. Note that subjects in Period 2 were responders from Period 1 (defined as ≥35% improvement in the ABC-C Irritability score from baseline to week 14 in Period 1) and as such may have even greater change than all subject in Period 1 as a result.

TABLE 14

| Summary of Mean Change from Baseline (BL) to Week 14 by ABC-C Irritability by Baseline PRAS Score | |
|---|---|
| Baseline PRAS Score | N, Change (SD) |
| >37 | 18, −14.7 (8.3) |
| ≤37 | 10, −7.6 (9.4) |

Collectively, this data shows that subjects having moderate to severe ASD and relatively high social avoidance and/or anxiety are more likely to show a reduction in irritability when treated with CBD.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method of treating a human suffering from moderate to severe autism spectrum disorder comprising transdermally administering via a gel or cream a therapeutically effective amount of purified cannabidiol to the human suffering from the autism spectrum disorder to effectively treat the autism spectrum disorder in the human in need thereof, wherein the gel or cream is administered to the upper arm.

2. The method according to claim 1, wherein the human has a baseline ABC-C irritability score of greater than 12.

3. The method according to claim 1, wherein the human has a baseline ABC-C$_{FXS}$ social avoidance score of greater than 5.

4. The method according to claim 1, wherein the human has a baseline Parent Rated Anxiety Scale for ASD (PRAS-ASD) score of greater than 25.

5. The method according to claim 1, wherein the human is diagnosed with moderate to severe ASD.

6. The method according to claim 1, wherein the human has an Autism Diagnostic Observation Schedule, 2$^{nd}$ Edition (ADOS-2) comparison score of greater than or equal to 3.

7. The method according to claim 1, wherein the CBD is administered transdermally.

8. The method according to claim 1, wherein the CBD is synthetic CBD.

9. The method according to claim 1, wherein the effective amount of CBD is a 250 mg total daily dose.

10. The method according to claim 1, wherein the effective amount of CBD is a 500 mg total daily dose.

11. The method according to claim 1, wherein the effective amount of CBD is a 750 mg total daily dose.

12. The method according to claim 1, wherein the effective amount of CBD is a 1000 mg total daily dose.

13. The method according to claim 1, wherein the effective amount is administered in two daily doses.

14. The method according to claim 1, wherein the CBD is administered in a pharmaceutically acceptable preparation that does not contain THC.

15. The method according to claim 1, wherein the human is also diagnosed with Fragile X Syndrome (FXS).

* * * * *